United States Patent
Farahani et al.

(10) Patent No.: US 8,503,748 B2
(45) Date of Patent: Aug. 6, 2013

(54) NONLINEAR RECURSIVE FILTER FOR MEDICAL IMAGE PROCESSING

(75) Inventors: Mohammad Hossein Farahani, Tehran (IR); Salar Sajedi Toighoun, Tabriz (IR); Mohammad Reza Ay, Tehran (IR); Saeed Sarkar, Tehran (IR)

(73) Assignee: Toseh Sanaye Tasvirbardari Parto Negar Persia, Tehran (IR)

( * ) Notice: Subject to any disclaimer, the term of this patent is extended or adjusted under 35 U.S.C. 154(b) by 188 days.

(21) Appl. No.: 13/196,664

(22) Filed: Aug. 2, 2011

(65) Prior Publication Data
US 2012/0027274 A1 Feb. 2, 2012

Related U.S. Application Data

(60) Provisional application No. 61/369,840, filed on Aug. 2, 2010.

(51) Int. Cl.
G06K 9/00 (2006.01)
G01T 1/161 (2006.01)

(52) U.S. Cl.
USPC ....... 382/128; 382/131; 382/132; 250/363.07

(58) Field of Classification Search
USPC ............... 382/128, 131, 132; 250/363.07
See application file for complete search history.

(56) References Cited

U.S. PATENT DOCUMENTS

| | | | | |
|---|---|---|---|---|
| 6,291,825 B1 * | 9/2001 | Scharf et al. | ................... | 250/369 |
| 6,525,323 B1 * | 2/2003 | Vesel et al. | ................... | 250/369 |
| 7,439,515 B2 * | 10/2008 | Bak | ................... | 250/369 |
| 7,966,155 B2 * | 6/2011 | Warburton et al. | ........... | 702/190 |
| 8,338,791 B2 * | 12/2012 | Proksa et al. | .................. | 250/369 |
| 8,340,377 B2 * | 12/2012 | McFarland et al. | ........... | 382/128 |
| 2003/0033097 A1 * | 2/2003 | Tanaka et al. | .................. | 702/60 |

OTHER PUBLICATIONS

Bolic et al., "Processing architecture for high count rate spectrometry with NaI(Tl) detector", FMTC 2008 IEEE, May 12-15, 2008.*
Joly et al., "An optimal filter based algorithm for PET detectors with digital sampling front-end", IEEE Transaction on Nuclear Science, vol. 57, No. 1, Feb. 2010.*

* cited by examiner

*Primary Examiner* — Anand Bhatnagar
*Assistant Examiner* — Soo Park

(57) ABSTRACT

A new system and method for medical image processing using a nonlinear recursive filter are disclosed. An input signal including two or more pulses received from a medical imaging system is sampled at a predetermined sampling rate. The maximum magnitude, i.e., peak, and/or the occurrence time of the maximum magnitude of the first pulse of the input signal is/are determined using a nonlinear recursive filter. Predicted magnitude values of the tail of the first pulse can be determined and subtracted from the input signal to correct for pileup before determining the maximum magnitude and/or occurrence time of the next pulses. A medical image can be reconstructed using the determined maximum magnitudes and/or the occurrence times of the maximum magnitudes of the pulses of the input signal. The nonlinear recursive filter can be implemented using one or more look-up tables.

19 Claims, 8 Drawing Sheets

NONLINEAR RECURSIVE FILTER FOR MEDICAL IMAGE PROCESSING

CROSS-REFERENCE TO RELATED APPLICATIONS

The present application claims the benefit of U.S. Provisional Patent Application Ser. No. 61/369,840, filed Aug. 2, 2010, which is incorporated herein by reference in its entirety.

SPONSORSHIP STATEMENT

This application has been sponsored by the Research Center for Science and Technology In Medicine and the Tehran University of Medical Sciences.

TECHNICAL FIELD

This application generally relates to medical image processing, and more particularly relates to a nonlinear recursive filter for medical image processing.

BACKGROUND

Data can conventionally be acquired from various data detectors, such as, for example, digital cameras, medical imaging systems, and nuclear detectors. The acquired data is typically processed to create a desired output, such as a two-dimensional or three-dimensional image. Although data acquisition in a simple imaging system does not usually suffer from any bottlenecks, typical data acquisition systems can be unreliable in high count rate applications. The unreliability of these systems is due to the relatively large dead-time for their imaging electronics, their difficulty in discriminating detector output pulses, their loss of useful data signals, their relatively low sampling rate, their relatively low pulse pileup recovery rate, and their relatively high susceptibility to noise.

As such, many efforts have been made to enhance signal quality and spatial resolution by reducing noise, pileup, baseline drift, and ballistic deficit. However, prior techniques were forced to compromise between their defects such that, for example, by improving the count rate, the signal quality was lowered. Moreover, signals acquired from photomultiplier tubes have noise and exponential decay time, which introduces imprecision in extraction of the pure signal. As such, a new system and method is needed to accurately distinguish pulse shapes in high count rate systems without the limitations of conventional data acquisition systems.

SUMMARY

A method for and system including at least one processor connected to at least one storage device can be configured for medical image processing using a nonlinear recursive filter. One or more look-up tables are created based on a mathematical pulse model. A baseline signal is sampled at a first predetermined sampling rate to extract two or more consecutive baseline samples, and a baseline value is determined based on the two or more consecutive baseline samples. An input signal is received from a medical imaging system including two or more pulses and the baseline value is subtracted from the input signal to form a baseline corrected input signal. The baseline corrected input signal is sampled at a second predetermined sampling rate to extract two or more consecutive samples within a first pulse of the baseline corrected input signal. The two or more consecutive samples within the first pulse of the baseline corrected input signal are compared with information stored in the one or more look-up tables to determine the maximum magnitude of the first pulse. The baseline corrected input signal is sampled at the second predetermined sampling rate to extract two or more consecutive samples within a second pulse of the baseline corrected input signal, where the second pulse of the baseline corrected input signal is temporally subsequent to and at least partially temporally overlaps with the first pulse of the baseline corrected input signal. At least two tail magnitudes of the first pulse of the baseline corrected input signal are predicted and subtracted from the temporally corresponding two or more consecutive samples within the second pulse of the baseline corrected input signal to correct the two or more consecutive samples within the second pulse of the baseline corrected input signal for pileup resulting from the first pulse of the baseline corrected input signal. The two or more consecutive samples within the second pulse of the baseline corrected input signal are compared with information stored in the one or more look-up tables to determine the maximum magnitude of the second pulse.

In some implementations, the mathematical pulse model can be $$f(a, t) = a \cdot t^a \cdot e^{-\frac{t}{\tau}},$$

wherein a is the peak magnitude of a pulse, t is time, $\alpha$ is a scaling factor, and $\tau$ is a decay constant.

In some implementations, a medical image can be reconstructed based on the maximum magnitude of the first pulse and the maximum magnitude of the second pulse and its presentation can be enabled. In some implementations, three or more two-dimensional look-up tables can be created based on the mathematical pulse model, where a first one of the three or more two-dimensional look-up tables can be used to determine the maximum magnitude of a pulse, a second one of the three or more two-dimensional look-up tables can be used to determine a first predicted pulse tail magnitude, and a third one of the three or more two-dimensional look-up tables can be used to determine a second predicted pulse tail magnitude. The one or more look-up tables can be created based on the mathematical pulse model before reception of the input signal from the medical imaging system.

In some implementations, the one or more look-up tables can be created based on an injective mathematical pulse model. The mathematical pulse model can be received from an operator, or identified based on comparisons between multiple predetermined pulse models and the input signal from the medical imaging system including the two or more pulses. The one or more look-up tables can be created based on a single decay mathematical pulse model.

In some implementations, the mean of the two or more consecutive baseline samples can be determined. The first predetermined sampling rate can be the same as the second predetermined sampling rate. The second predetermined sampling rate can be between one-half of the rise time of the first pulse and lower than the total pulse duration of the first pulse.

In some implementations, the two or more consecutive samples within the first pulse of the baseline corrected input signal can be compared with information stored in one look-up table to determine the maximum magnitude of the first pulse, and the two or more consecutive samples within the first pulse of the baseline corrected input signal can be compared with information stored in another look-up table to determine the time of occurrence of the maximum magnitude of the first pulse.

In some implementations, the two or more consecutive samples within the first pulse of the baseline corrected input signal can be compared with information stored in at least two look-up tables to determine the at least two tail magnitudes of the first pulse. A first tail magnitude can be predicted occurring at one sampling period following the two or more consecutive samples within the first pulse of the baseline corrected input signal and a second tail magnitude can be predicted occurring at two sampling periods following the two or more consecutive samples within the first pulse of the baseline corrected input signal. The first tail magnitude of the first pulse of the baseline corrected input signal can occur at the same time as the first sample within the second pulse of the baseline corrected input signal, and the second tail magnitude of the first pulse of the baseline corrected input signal can occur at the same time as the second sample within the second pulse of the baseline corrected input signal.

Details of one or more implementations of the nonlinear recursive filter for medical image processing are set forth in the accompanying drawings and the description below. Other aspects that can be implemented will be apparent from the description and drawings, and from the claims.

DESCRIPTION OF DRAWINGS

Like reference symbols indicate like elements throughout the specification and drawings.

DETAILED DESCRIPTION

A new system and method for medical image processing using a nonlinear recursive filter are disclosed. An input signal including two or more pulses received from a medical imaging system is sampled at a predetermined sampling rate. The maximum magnitude, i.e., peak, and/or the occurrence time of the maximum magnitude of the first pulse of the input signal is/are determined using a nonlinear recursive filter. Predicted magnitude values of the tail of the first pulse can be determined and subtracted from the input signal to correct for pileup before determining the maximum magnitude and/or occurrence time of the next pulses. A medical image can be reconstructed using the determined maximum magnitudes and/or the occurrence times of the maximum magnitudes of the pulses of the input signal. The nonlinear recursive filter can be implemented using one or more look-up tables.

Figure 1A:
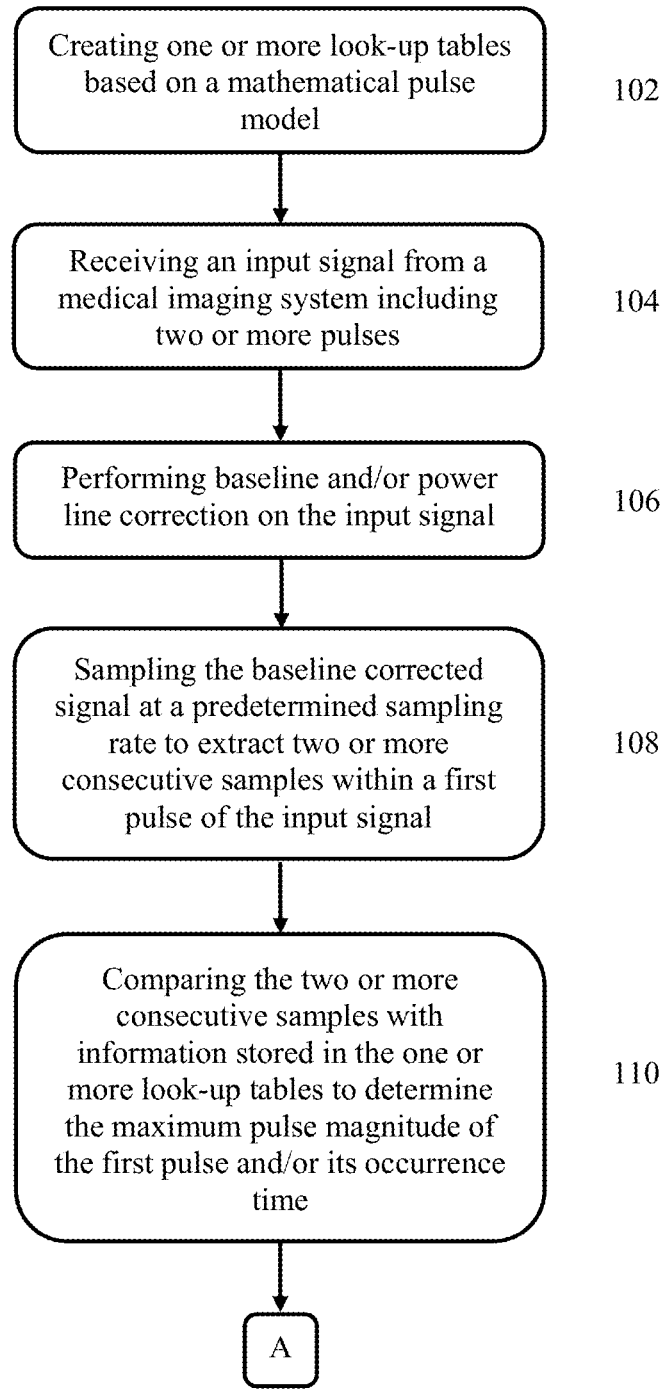
FIGS. 1*a-b* illustrate an example method for medical image processing using a nonlinear recursive filter.
Figure 1B:
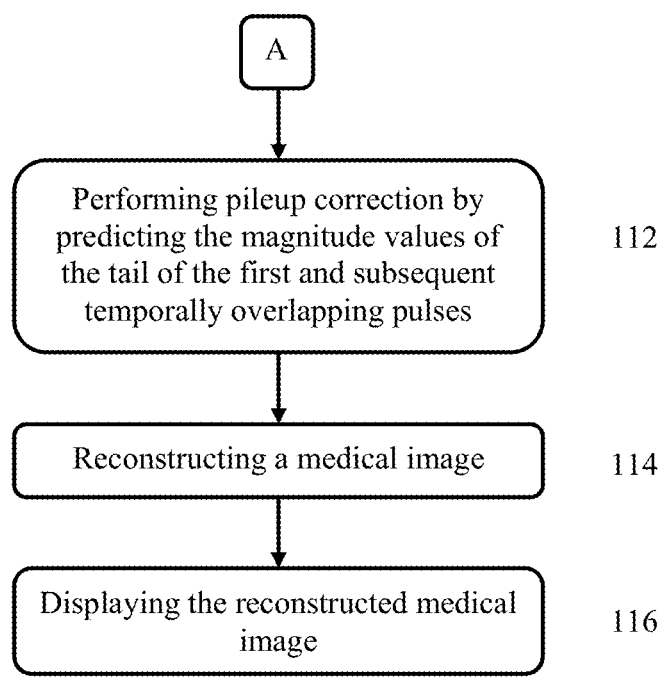

Referring to FIGS. 1*a-b*, a method for medical image processing using a nonlinear recursive filter is disclosed. One or more look-up tables (hereinafter "LUTs") can be created based on a mathematical pulse model (step 102). The nonlinear recursive filter is based on the principle that the response of an imaging detector follows a deterministic shape pattern that only varies with time and magnitude. More simply, it is assumed that the shape of each pulse of an input signal only scales with magnitude and moves with time. It follows, then, that the magnitudes of two consecutive samples within a pulse will depend on the maximum magnitude of the pulse and the first sampling time (as the second sampling time is a sum of the first sampling time and the sampling period).

Each pulse can be modeled using an injective mathematical equation, e.g., a one-to-one function, based on, for example, the type of medical imaging system and/or detector of the medical imaging system used to capture the input signal. In some implementations, single exponential decay equations and double exponential decay equations can be used to model scintillation detector pulses. Because the mathematical equations are injective, by knowing the magnitudes of the two consecutive samples, the first sampling time and the sampling period, the maximum pulse magnitude and its time of occurrence can be determined. Based on the maximum pulse magnitude and/or its time of occurrence, the exact mathematical model of the pulse shape can be determined, as explained in greater detail below.

Figure 2:
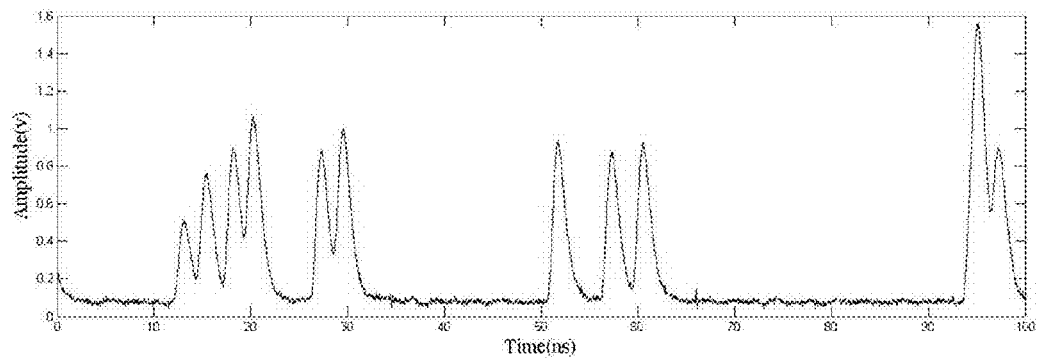
FIG. 2 illustrates an example signal received from a gamma camera of a medical imaging system.

Referring to FIG. 2, an input signal is received from a gamma camera of a nuclear medicine imaging system is illustrated. In some implementations, an operator of the system can identify the equations to use to model the detector output. In other implementations, two or more known models can be cross-correlated with the detector output, such as the signal illustrated in FIG. 2, to identify the model with the highest correlation for use as the pulse model. An injective mathematical function that can model each pulse of the input signal illustrated in FIG. 2 is provided by EQ. 1:

$$f(a, t) = a \cdot t^{\alpha} \cdot e^{-\frac{t}{\tau}} \qquad (1)$$

where $\alpha$ is a power scaling factor and $\tau$ is a decay constant based on the particular medical imaging system and detector used to capture the input signal. In some implementations, the power scaling factor and the decay constant can be determined by, for example, curve fitting performed automatically or manually by an operator. For example, in some implementations, $\alpha$ can equal 3 and $\tau$ can equal 185 ns. The variable a represents the maximum pulse magnitude and t represents time. As such, according to EQ. 1, to determine the maximum pulse magnitude a and its time of occurrence $t_a$, the inverse of EQ. 1 must be independently solved once for both a and $t_a$, as shown in EQS. 2-4:

$$(a, t_a) = f^{-1}(x, y) \qquad (2), \text{where}$$

$$a = f_0(x, y) \qquad (3), \text{and}$$

$$t_a = f_1(x, y) \qquad (4),$$

where x represents the magnitude of a first sample and y represents the magnitude of a second sample within a first pulse of the input signal. Following some algebraic operations, a and $t_a$ can be determined according to EQS. 5-7:

$$a = \frac{x}{t_a^{\alpha} \cdot e^{-\frac{t_a}{\tau}}}, \text{ and} \qquad (5)$$

-continued $$t_a = \frac{c \cdot t_s}{1-c}, \text{ where} \tag{6}$$

$$c = e^{-\frac{t_s}{T \cdot \alpha}} \cdot \left(\frac{x}{y}\right)^{\frac{1}{\alpha}}. \tag{7}$$

Figure 3:
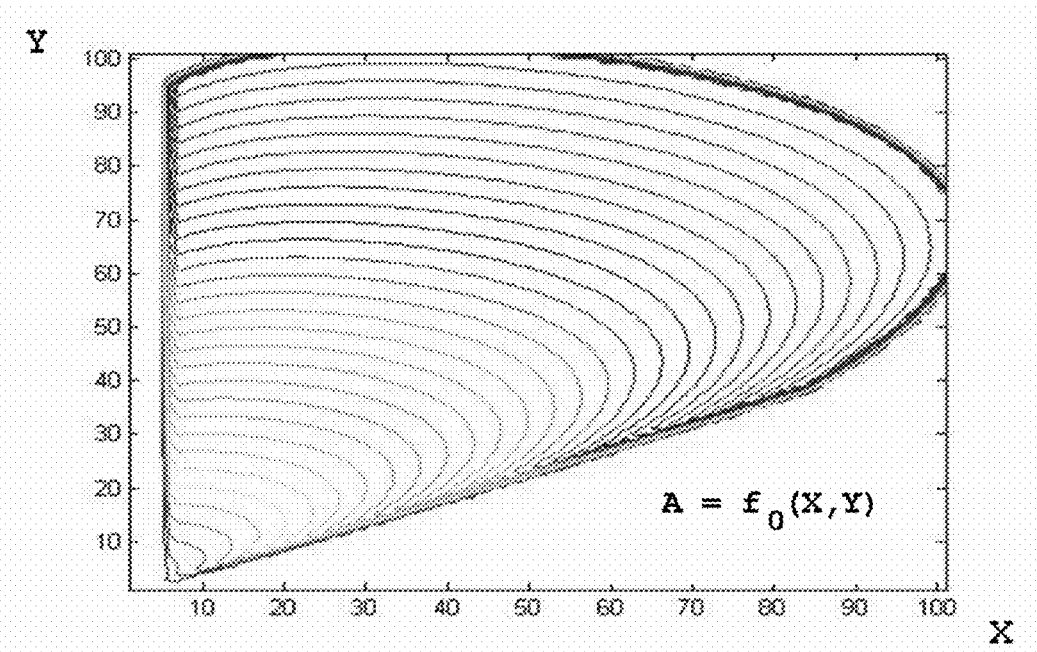
FIG. 3 illustrates an example map of peak pulse magnitudes as a function of two sequential detector samples.

Due to the computation complexity of solving EQs. 5-7 for each pulse of an input signal, especially in real-time configurations, it is more practical to implement these equations by way of 2-dimensional LUTs. The LUTs can map the (x,y) sample pair to values for a and $t_a$. For example, a map of the function a=$f_0$(x,y) (EQ. 3) is illustrated in FIG. 3. Each one of the many curves in FIG. 3 corresponds to a locus of all x and y values corresponding to a single pulse peak for a pulse model. A similar map and corresponding LUT can be constructed for $t_a$.

Moreover, 2-dimensional LUTs can be constructed for predicting pulse tail magnitudes following the pulse peak. For example, if three pulse tail magnitudes are necessary for pileup correction, as explained in greater detail below with reference to step 112, three LUTs can be constructed to predict the pulse tail magnitudes at three consecutive sampling periods using the known pulse model. In some implementations, the input of the LUTs used to predict pulse tail magnitudes can be the (x,y) sample pair that is also used to determine the maximum magnitude of the pulse and/or its occurrence time, as explained in greater detail with reference to FIG. 5.

In some implementations, the construction of the LUTs can performed following sampling of the input signal in step 108 using known (x,y) values. However, to construct the LUTs before imaging, rather than using a range of (x,y) points to determine the corresponding values of a and $t_a$, a reverse method can be implemented by sweeping a range of (a, $t_a$) pairs to calculate corresponding (x,y) points. The sweeping range for $t_a$ should be at least twice the sampling period $t_s$ to ensure that all possible (x,y) points within a pulse will be included in the LUTs. The sweeping resolution should be small enough to avoid any holes in the LUTs and the estimations for a and $t_a$ can be interpolated to improve the resolution of the LUTs. In addition, in some implementations, the small magnitude values, such as, for example, magnitudes below ten percent of the peak magnitude a of a pulse, for x and y can be removed from the LUTs to improve noise robustness of the nonlinear filter.

The resolutions of the estimations for a and $t_a$ depend on the resolution of the LUTs. In particular, the resolutions of the values of x and y in the LUTs directly correlate to the resolution of the estimations of a and $t_a$. In implementation, for example, if the values of x and y have an 11-bit resolution, their corresponding LUT would require at least 44 megabits to be stored.

An input signal is received from a medical imaging system including two or more pulses (step 104). The input signal can be, for example, any voltage and/or current magnitude that can be sampled over time. The input signal can be received from a medical imaging detector and/or from another source, such as, a digital storage medium. In some implementations, the detector can be one or more of the following types of detectors: nuclear detectors, such as, for example, gaseous, scintillation, and/or semiconductor detectors; nuclear medicine imaging systems, such as, for example, gamma and/or x-ray detection systems; single photon emission computed tomography (hereinafter "SPECT") systems; positron emission tomography (hereinafter "PET") systems; computed tomography (hereinafter "CT") systems; time-of-flight PET systems; spectroscopy systems; and/or industrial radiography systems.

The medical imaging system can include a scintillation detector, such as a gamma camera, and one or more photomultiplier tubes that output a series of pulses whose magnitudes represent the magnitude of energy, e.g., gamma rays, deposited on the scintillation detector. In some implementations, the input signal can include a finite number of pulses and be time-invariant. An example of such an input signal received from a medical imaging system is illustrated in FIG. 2, which shows a series of spikes measured as voltages over time.

Next, baseline and/or power line correction can be performed on the input signal (step 106). Before receiving the input signal in step 104, a series of baseline samples can be collected at a predetermined sampling rate to determine the baseline voltage of the system due to noise and/or power line interference. The predetermined sampling rate can be the same sampling rate used to sample the input signal or a different sampling rate. In some implementations, two or more consecutive samples can be collected before the input signal is received and averaged to determine the baseline voltage. Then, the magnitude of the baseline voltage can be subtracted from the input signal before sampling in step 108 to perform baseline correction.

While in some implementations, the baseline samples are averaged to determine the average baseline of the system, in other implementations, a weighted average, a moving average, or a median of the baseline samples can be calculated and used as the baseline of the system. In some implementations, the average baseline can be calculated every time the system is turned on, while in other implementations, the average baseline can be calculated every time before reception of an input signal, while in yet other implementations, the average baseline can be calculated at predetermined time intervals.

Figure 4:
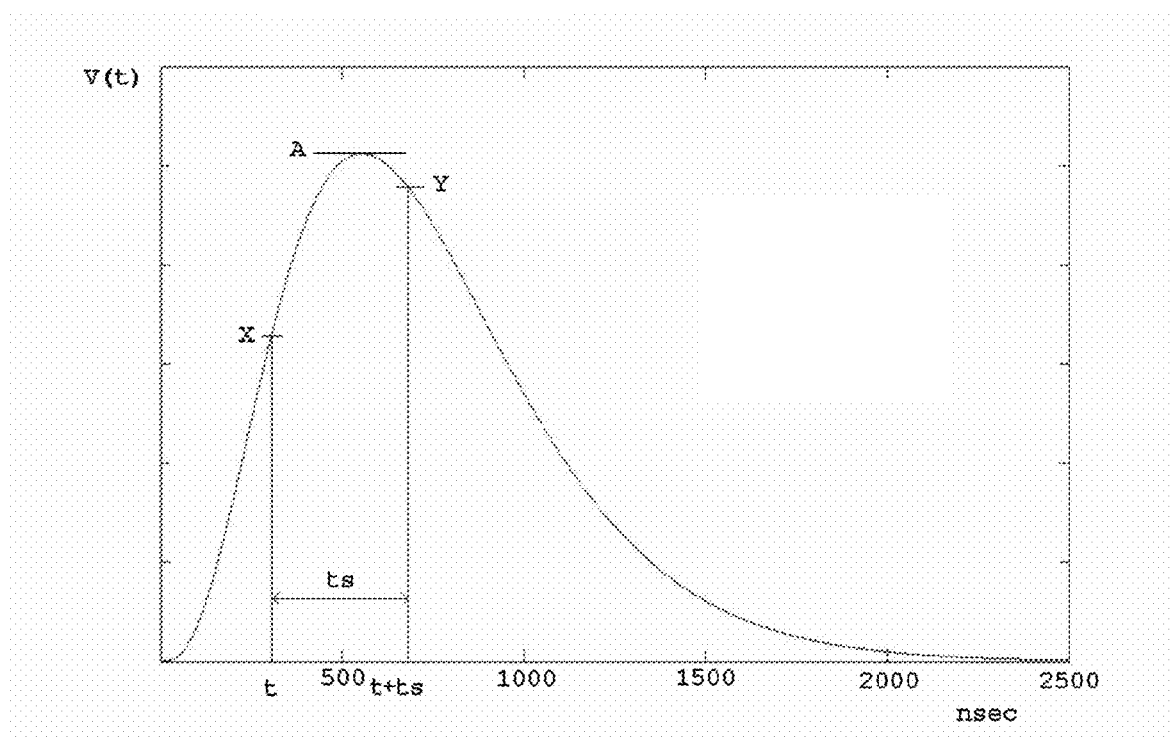
FIG. 4 illustrates an example pulse showing digital sampling details.

The baseline corrected signal is then sampled at a predetermined sampling rate to extract two or more consecutive samples within a first pulse of the input signal (step 108). Referring to FIG. 4, for example, a pulse of the input signal is consecutively sampled at a first time t and a second time t+$t_s$, where $t_s$ is the sampling period and the inverse of the sampling rate. A single pulse within a signal received from a detector is typically composed of a rising edge, a peak, and a tail. The magnitude x corresponds to the detected voltage at time t during the rising edge of the pulse and the magnitude y corresponds to the detected voltage at time t+$t_s$ during the tail of the pulse. The magnitude a corresponds to the detected voltage at the peak of the pulse. As such, the first extracted sample can correspond to the point ($t_x$, x) and the second extracted sample can correspond to the point ($t_x$+$t_s$, y) in FIG. 4.

The sampling period $t_s$ can be selected based on the characteristics of the input signal and the hardware capabilities of the image reconstruction system. For example, with respect to the hardware capabilities, the capacity and speed of the analog-to-digital converter of the system and the capacity and speed of the memory of the system should be used as limits for the sampling period $t_s$.

With respect to the characteristics of the input signal, by reducing the sampling period $t_s$, the noise sensitivity of the nonlinear recursive filter of this application increases because the difference between the magnitudes of samples captured too close to one another may be significantly based on noise. In some implementations, the sampling period $t_s$ can be greater than the one-half of the rise time of the pulse and lower than the total pulse duration. Between these two limits, however, the sampling period $t_s$ should selected in light of the desired pileup recovery ratio and robustness. Preferably, the sampling period $t_s$ can be close to the rise time of the pulse.

In addition, depending on the specific pulse model, a particular number of samples within the tail of the pulse are needed to correct for pileup errors and, therefore, the sampling period should be low enough to capture the particular number of samples within the tail of the pulse. Moreover, because of the nonlinear behavior of the filter, the sampling rate can be selected below the Nyquist rate without missing valuable information within the signal. In some implementations where the rise time of a pulse is 550 ns and can be generally modeled by EQ. 1, for example, the sampling period $t_s$ with the best performance is 333 ns.

The maximum magnitude of the first pulse a and/or its occurrence time $t_a$ are then determined based on the comparison of the two or more consecutive samples with the information stored in the LUTs (step 110). In particular, using the x and y values sampled from the input signal in step 104, the values of a and/or $t_a$ can be estimated without computation complexity by referring to the appropriate LUTs. For example, the values of x and y can be compared with a LUT based on the maps of the maximum magnitudes illustrated in FIG. 3 to determine the maximum magnitude of the first signal. In some implementations, only the value of a may be determined, while in other implementations only the value of $t_a$ may be determined, while yet in other implementations, both the value of a and $t_a$ can be determined. For example, in some medical imaging systems, such as those that employ gamma cameras, the time of occurrence of the peak magnitude $t_a$ is not necessary for image reconstruction, whereas in others, such as time-of-flight PET systems, $t_a$ is necessary for image reconstruction.

Next, the input signal is corrected for pileup by predicting the magnitude values of the tail of the first and subsequent temporally overlapping pulses, which are then subtracted from the baseline corrected input signal (step 112). The tail of a pulse can return to its baseline in various forms after passing its peak and the fall time is usually longer than the rise time due to the physical characteristics of data detectors. This phenomenon can significantly affect the interpretation of subsequent pulses in an input signal that are temporally close to a previous pulse, as the rising edge of the subsequent pulse can temporally overlap with the falling edge of a prior pulse, resulting in pileup. Therefore, to remove the effects of pileup, the magnitude values of the tail of the temporally overlapping pulses must be predicted and subtracted from the baseline corrected input signal.

The predicted pulse tail magnitudes can be determined by comparing the values of x and y with appropriate LUTs based on the known pulse model. Specifically, by knowing the pulse shape and the values of the maximum pulse magnitude a, subsequent magnitudes of the pulse at the system sampling periods can be predicted by $z = f_n(a, t+n*t_s)$, where n is an integer greater than or equal to 2.

Figure 5:
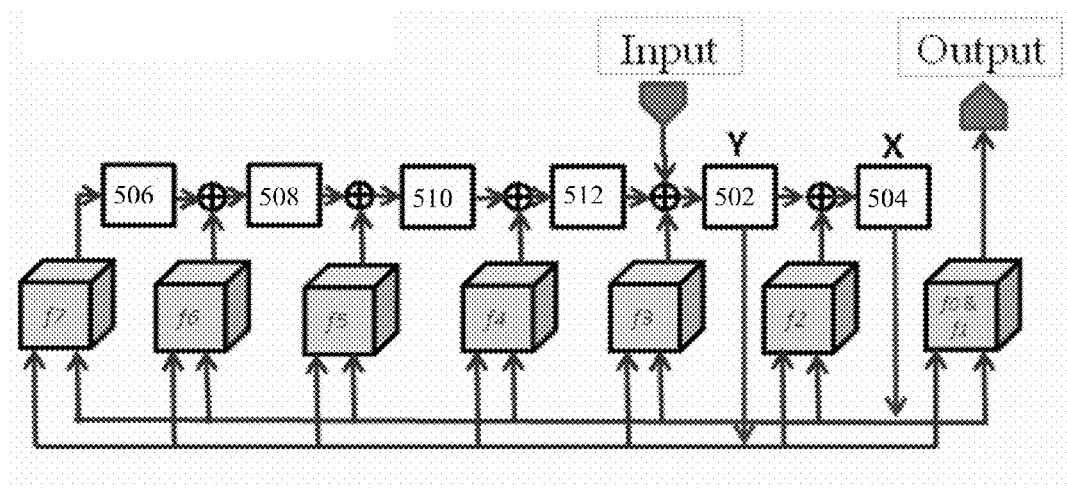
FIG. 5 illustrates an example block diagram of an implementation of the nonlinear recursive filter.

For example, referring to FIG. 5, the input signal is sampled at a predetermined sampling period $t_s$ and input into a series of shift registers 502-512. Initially, the shift registers 502-512 are set to zero. The first sample magnitude x for the first pulse is input into shift register 502. Because shift register 504 is initially set to zero, the value of x is not adjusted before it is shifted to the next shift register after the sampling period. Next, the value of the first sample magnitude x is shifted into shift register 504 and the second sample magnitude y for the first pulse is input into shift register 502. Using the values of x and y in shift registers 504 and 502, respectively, the values of the maximum pulse magnitude a and/or its time of occurrence $t_a$ can be determined by functions $f_0$ and $f_1$ corresponding to EQS. 3 and 4, respectively, using the LUTs constructed in step 102. The values of maximum pulse magnitude a and/or its time of occurrence $t_a$ are then output for use in image reconstruction.

Simultaneously, the value of x and y in shift registers 504 and 502 are fed into functions $f_2$ to $f_7$ to determine the predicted values of the pulse tail at subsequent times that are a multiple of the sampling period. For example, the function $f_2$ can comprise of a LUT to predict the magnitude of the pulse at a time equal to twice the sampling period following the time of the first sample. Similarly, function $f_3$ can comprise of a LUT to predict the magnitude of the pulse at a time equal to three times the sampling period following the time of the first sample, and so forth. In some implementations, such as the implementation illustrated in FIG. 5, the predicted magnitudes are then turned negative and added to the magnitude value being shifted in the next shift register using an adder. In other implementations, the predicted magnitudes remain positive and are subtracted from the magnitude value being shifted in the next shift register using a subtracter, so that the sum of the tail magnitudes of multiple pulses at the same time is determined.

For example, in the implementation of FIG. 5, once the two samples for the first pulse x and y are determined, the predicted magnitude of the sixth pulse tail calculated by the function $f_7$ is turned negative and input into shift register 506, the predicted magnitude of the fifth pulse tail calculated by the function $f_6$ is turned negative and input into shift register 508, the predicted magnitude of the fourth pulse tail calculated by the function $f_5$ is turned negative and input into shift register 510, the predicted magnitude of the third pulse tail calculated by the function $f_4$ is turned negative and input into shift register 512, the predicted magnitude of the second pulse tail calculated by the function $f_3$ is turned negative and added to the sample magnitude of the baseline corrected input signal being input and then input into shift register 502, and the predicted magnitude of the first pulse tail calculated by the function $f_2$ is turned negative and added to the value stored in shift register 502 and then input into shift register 504.

Following the next sampling period, the magnitudes of the tail predictions of the next pulse are turned negative and added to the corresponding tail predictions of the prior pulse so that the cumulative tail magnitudes are determined. For example, the sixth pulse tail of the first pulse from shift register 506 is added to the fifth pulse tail of the second pulse from function $f_6$ and stored in shift register 508. Similarly, following the next sampling time period, the fourth pulse tail of the third pulse is added to the value stored in shift register 508, which is a sum of the sixth pulse tail of the first pulse and the fifth pulse tail of the second pulse, and input into shift register 510.

As such, the cumulative tail magnitudes of six pulses are subtracted from each x sample in shift register 504, so that the actual magnitude contributed by the pulse being sampled is used to determine the maximum pulse magnitude. The number of pulse tail predictions used to correct for pileup depends on the model of the pulse. In particular, the number of pulse tail predictions should be such that the last pulse tail prediction has negligible magnitude, i.e., the pulse tail does not significantly contribute to pileup and is close to zero. For example, if a pulse tail requires a period of six times the sampling period to have a negligible tail magnitude, then six pulse tail predictions are necessary to correct for pileup. In some implementations, between three and nine pulse tail predictions may be necessary for pileup correction.

Following pileup correction, the medical image is reconstructed based on the maximum magnitudes of the pulses and/or their occurrence times (step 114). The algorithm used for image reconstruction depends on the particular imaging system and/or type of image to be reconstructed. In some implementations, filtered back projection techniques can be used, while in other implementations, the stochastic expectation maximization ("SEM") iterative technique can be used to reconstruct the medical image in step 114. Preferably, for gamma ray detectors, the maximum-likelihood expectation maximization ("MLEM") iterative technique can be used for image reconstruction.

Finally, the reconstructed medical image can be displayed (step 116). The reconstructed medical image can be displayed on, for example, a display device, such as a monitor or LCD screen, for displaying the medical image to a user. In some implementations, presentation of the medical image on a display can be enabled by, for example, sending the medical image to a system capable of displaying the medical image and/or storing the medical image on a computer-readable storage medium.

Figure 6:
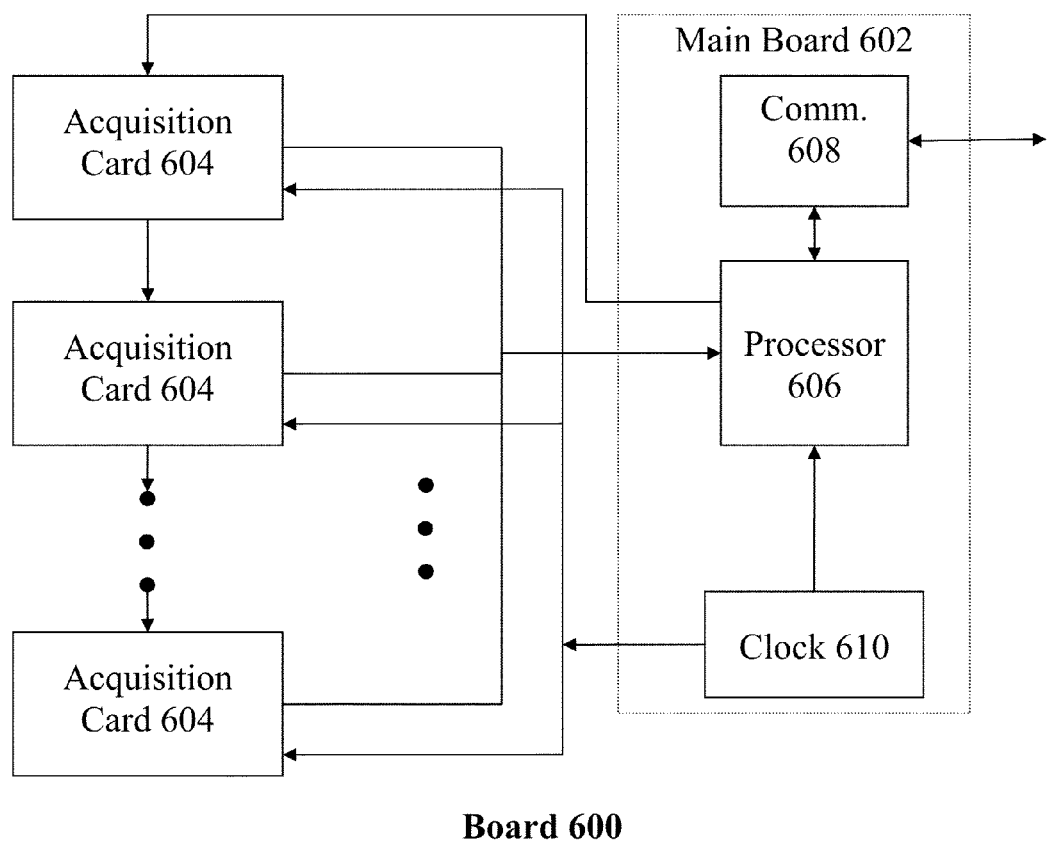
FIG. 6 illustrates an example schematic diagram of a board for data acquisition and system control.

FIG. 6 shows an example schematic diagram of an example board 600 for data acquisition and system control for a scintillation detector imaging system, such as a gamma ray detector imaging system. The board 600 includes a main board 602 that is connected to one or more data acquisition cards 604. The main board 602 includes at least one processor 606, a communication interface 608, and a clock 610. In some implementations, the main board 602 can also include a memory. Each of the components of the board 600 can, for example, be interconnected using a device bus. Each of the data acquisition cards 604 are connected to a photomultiplier tube of the scintillation detector imaging system to capture an output from the photomultiplier tube. As such, in spectroscopy applications, only one data acquisition card 604 is required.

The processor 606 is capable of processing instructions for execution within the scintillation detector imaging system. For example, the processor can be capable of creating the LUTs, managing the data acquisition cards 604, and/or reconstructing the medical image. For example, in some implementations, the processor 606 can be capable of determining the pulse peak and/or its time of occurrence based on the pileup corrected data from each of the data acquisition cards 604. In other implementations, the pulse peak and/or its time of occurrence can be determined in the data acquisition cards 604. The processor 606 can be capable of determining the location of a pulse among several photomultiplier tubes for image reconstruction. The processor 606 can also be capable of other forms of data correction, such as, for example, uniformity correction, scatter correction, and/or attenuation correction. In some implementations, the processor 606 is a single-threaded processor, while in other implementations, the processor 606 is a multi-threaded processor. For example, the processor 606 can be a field programmable gate array ("FPGA") processor.

The communication interface 608 makes a direct or indirect connection to a main system, such as a computer used by a user. The communications interface 608 can link to the computer through, for example, a wired or wireless pathway. In some implementations, the communications interface 608 can be a universal serial bus ("USB") interface. The clock 610 synchronizes the data acquisition cards 604 and the main board 602. The data output from each of the data acquisition cards 604 is transferred to the main board 602 by a parallel or, preferably, a serial interface.

Figure 7:
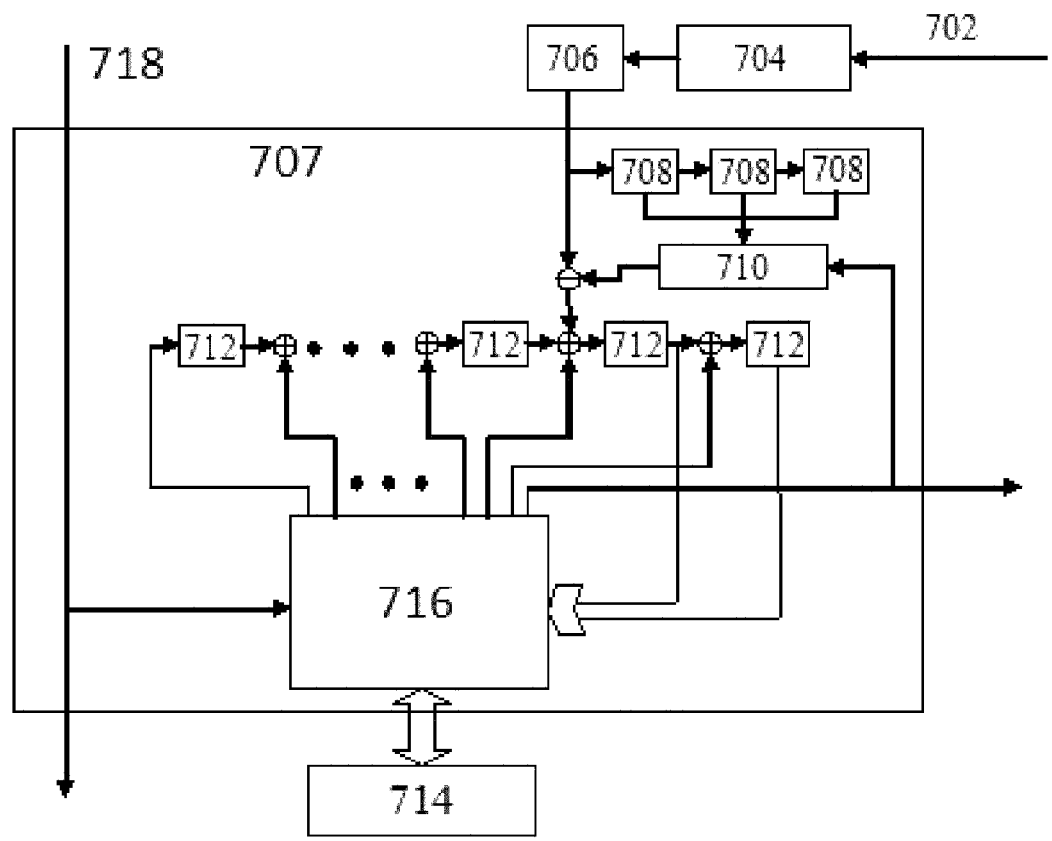
FIG. 7 illustrates an example schematic diagram of a data acquisition board.

FIG. 7 shows a schematic diagram of an example data acquisition board 604. Initially, an analog signal 702 from a photomultiplier tube is input to an amplifier 704 to amplify the analog signal 702 to a voltage suitable for analog-to-digital ("A/D") conversion. An A/D converter 706 converts the analog input signal 702 to a series of discrete points that are input into a processor 707. The processor 707 includes two or more and, preferably, three shift registers 708 that store consecutive baseline samples of the input signal before the start of data acquisition. A baseline predictor 710 calculates the mean of the consecutive baseline samples to determine a baseline for the system, which is subtracted from the input signal, resulting in a baseline corrected input signal. The baseline corrected input signal is then sampled at a predetermined sampling frequency and the samples are input into the shift registers 712, which operate as described with reference to FIG. 5. The LUTs for determining the maximum pulse magnitude and/or its occurrence time, and for predicting the pulse tail magnitudes, in addition to other system information are stored in a memory 714. The memory 714 can be a read-only memory and/or a random access memory. For example, a synchronous dynamic random access memory can store the LUTs. In some implementations, if one LUT is used to determine the pulse peak magnitude and nine other LUTs are used to predict nine pulse tail magnitudes, then 440 Mb of storage space in the memory 714 is necessary to the store the LUTs.

The memory 714 is connected to a memory controller 716 that is capable of writing the LUTs and/or other data in memory 714. The LUTs and/or other data are received from the main board 602 via the bus 718. In some implementations, because the same LUTs are stored on each of the data acquisition cards 604, the memories 714 of the data acquisition cards 604 can be filled in parallel, while in other implementations, the memories 714 of the data acquisition cards 604 can be filled in a round robin, i.e., chain, manner. In the round robin technique, the first data acquisition card 604 in the chain can receive the LUT data and then pass the LUT data to the next card after storing it.

In some implementations, the memory controller 716 also receives the input samples from the shift registers 712 and compares the sample values to the LUTs stored in the memory 714 to determine the peak magnitude of a pulse and/or its time of occurrence. The memory controller 716 then outputs the peak magnitude and/or its time of occurrence to the processor 606 for determining, for example, the location of the pulse. In some implementations, the processor 606 can weight the inputs received from the memory controllers 716 so that different data acquisition cards 604 are assigned different weights and, therefore, different significances.

In one implementation, sample input signals including two or more pulses were created using a monte-carlo method at various count rates and used to test the effectiveness of the nonlinear recursive filter disclosed above. The sampling period used was 300 ns and the pulse was modeled by $$f(t) = at^{4.3} e^{\frac{t}{160ns}}.$$

The full-width half-max ("FWHM") of a pulse as a percentage of pulse width and the registered count ratio of the nonlinear recursive filter were measured to determine performance of the filter. The lower the FWHM percentage of the detected pulse, the more the detected pulse resembles a spike. Also, the higher the registered count ratio of the input signal, the lower the number of undetected, i.e., dropped, pulses. The performance of the nonlinear recursive filter at different count rates is shown in TABLE 1 below:

| Count Rate (kcps) | FWHM (%) | Registered/Total Count |
|---|---|---|
| 50 | 11.69 | 0.958 |
| 100 | 11.69 | 0.954 |
| 200 | 11.76 | 0.907 |
| 300 | 12.00 | 0.852 |
| 400 | 12.46 | 0.804 |
| 500 | 12.69 | 0.760 |
| 750 | 13.30 | 0.654 |
| 1,000 | 14.53 | 0.562 |
| 1,250 | 16.92 | 0.476 |

As shown in TABLE 1, as the count rate of the input signal is increased from 50 kcps to 1,250 kcps, the detected pulse becomes wider and, thus, less resembles a pulse. In addition, the registered count rate ratio decreases from 0.958 at a count rate of 50 kcps to 0.476 at a high count rate of 1,250 kcps. However, at a count rate of up to 500 kcps, the registered count rate is 0.760, meaning that less than 25% of the pulses were dropped by the nonlinear recursive filter.

Figure 8:
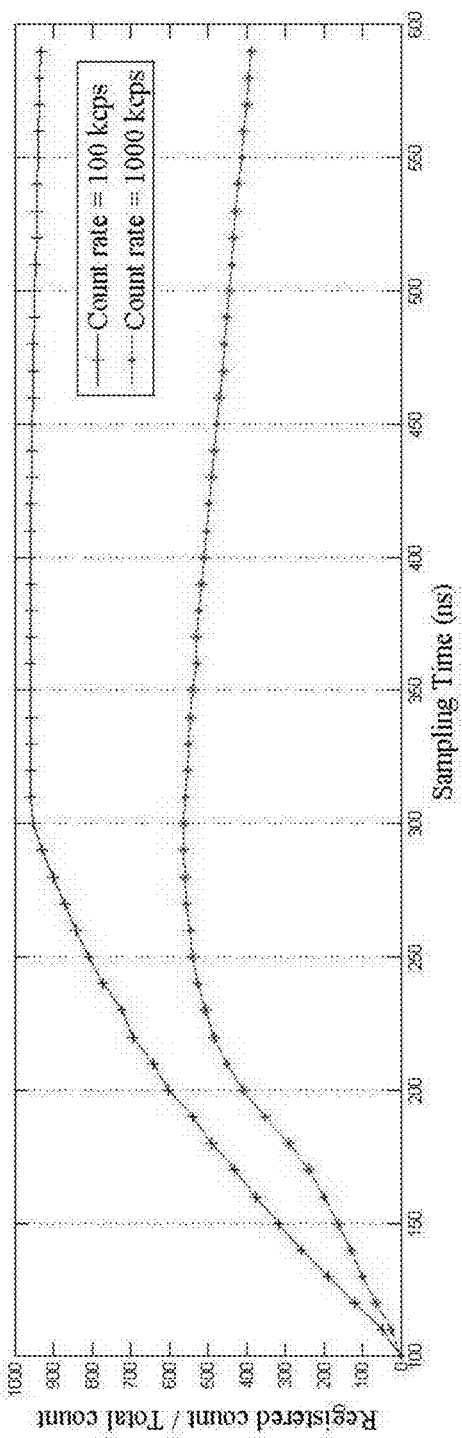
FIG. 8 illustrates a chart of the registered count rate ratio as a function of sampling period.

Referring to FIG. 8, a chart of the registered count rate ratio as a function of the system sampling period $t_s$ is illustrated. As shown in FIG. 8, the sampling period having the highest registered count rate ratio is about 300 ns. In addition, due to the nonlinear nature of the filter, as the sampling period $t_s$ is doubled to 600 ns, the registered count rate ratio decreases by less than 20%.

The nonlinear recursive filter provides several advantages, such as, for example, a relatively high count rate capability, powerful pileup detection and, resultantly, a relatively high pileup recovery rate, the ability to employ a sampling rate below the Nyquist sampling rate due to the nonlinearity of the filter, a stable image resolution even at high detector count rates, a relatively low susceptibility to noise, the ability for real-time baseline restoration, a relatively fast pulse response detection, the ability for high resolution differential time-of-flight detection, the customization of the filter for various signal shapes, a relatively high system flexibility for various detection applications, and a relatively low cost and low complexity implementation.

It is to be understood that the disclosed implementations are not limited to the particular processes, devices, and/or apparatus described which may, of course, vary. It is also to be understood that the terminology used herein is for the purpose of describing particular embodiments only, and is not intended to be limiting. As used in this application, the singular forms "a," "an," and "the" include plural referents unless the content clearly indicates otherwise.

Reference in the specification to "one implementation" or "an implementation" means that a particular feature, structure, characteristic, or function described in connection with the implementation is included in at least one implementation herein. The appearances of the phrase "in some implementations" in the specification do not necessarily all refer to the same implementation.

Accordingly, other embodiments and/or implementations are within the scope of this application.

What is claimed is:

1. A method for medical image processing using a nonlinear recursive filter, comprising:
creating one or more look-up tables based on a mathematical pulse model;
sampling a baseline signal at a first predetermined sampling rate to extract two or more consecutive baseline samples;
determining a baseline value based on the two or more consecutive baseline samples;
receiving an input signal from a medical imaging system including two or more pulses;
subtracting the baseline value from the input signal to form a baseline corrected input signal;
sampling the baseline corrected input signal at a second predetermined sampling rate to extract two or more consecutive samples within a first pulse of the baseline corrected input signal;
comparing the two or more consecutive samples within the first pulse of the baseline corrected input signal with information stored in the one or more look-up tables to determine the maximum magnitude of the first pulse;
sampling the baseline corrected input signal at the second predetermined sampling rate to extract two or more consecutive samples within a second pulse of the baseline corrected input signal, wherein the second pulse of the baseline corrected input signal is temporally subsequent to and at least partially temporally overlaps with the first pulse of the baseline corrected input signal;
predicting at least two tail magnitudes of the first pulse of the baseline corrected input signal;
subtracting the at least two tail magnitudes of the first pulse of the baseline corrected input signal from the temporally corresponding two or more consecutive samples within the second pulse of the baseline corrected input signal to correct the two or more consecutive samples within the second pulse of the baseline corrected input signal for pileup resulting from the first pulse of the baseline corrected input signal; and
comparing the two or more consecutive samples within the second pulse of the baseline corrected input signal with information stored in the one or more look-up tables to determine the maximum magnitude of the second pulse.

2. The method of claim 1, further comprising:
reconstructing a medical image based on the maximum magnitude of the first pulse and the maximum magnitude of the second pulse; and
enabling presentation of the reconstructed medical image.

3. The method of claim 1, wherein creating the one or more look-up tables based on the mathematical pulse model comprises creating three or more two-dimensional look-up tables based on the mathematical pulse model.

4. The method of claim 3, wherein a first one of the three or more two-dimensional look-up tables is used to determine the maximum magnitude of a pulse, a second one of the three or more two-dimensional look-up tables is used to determine a first predicted pulse tail magnitude, and a third one of the three or more two-dimensional look-up tables is used to determine a second predicted pulse tail magnitude.

5. The method of claim 1, wherein creating the one or more look-up tables based on the mathematical pulse model comprises creating the one or more look-up tables based on an injective mathematical pulse model.

6. The method of claim 1, wherein creating the one or more look-up tables based on the mathematical pulse model comprises receiving the mathematical pulse model from an operator.

7. The method of claim 1, wherein creating the one or more look-up tables based on the mathematical pulse model comprises identifying the mathematical pulse model based on comparisons between multiple predetermined pulse models and the input signal from the medical imaging system including the two or more pulses.

8. The method of claim 1, wherein creating the one or more look-up tables based on the mathematical pulse model comprises creating the one or more look-up tables based on a single decay mathematical pulse model.

9. The method of claim 1, wherein determining the baseline value based on the two or more consecutive baseline samples comprises determining the mean of the two or more consecutive baseline samples.

10. The method of claim 1, wherein the first predetermined sampling rate is the same as the second predetermined sampling rate.

11. The method of claim 1, wherein the second predetermined sampling rate is between one-half of the rise time of the first pulse and lower than the total pulse duration of the first pulse.

12. The method of claim 1, wherein comparing the two or more consecutive samples within the first pulse of the baseline corrected input signal with information stored in the one or more look-up tables to determine the maximum magnitude of the first pulse comprises comparing the two or more consecutive samples within the first pulse of the baseline corrected input signal with information stored in one look-up table to determine the maximum magnitude of the first pulse and comparing the two or more consecutive samples within the first pulse of the baseline corrected input signal with information stored in another look-up table to determine the time of occurrence of the maximum magnitude of the first pulse.

13. The method of claim 1, wherein predicting the at least two tail magnitudes of the first pulse of the baseline corrected input signal comprises comparing the two or more consecutive samples within the first pulse of the baseline corrected input signal with information stored in at least two look-up tables to determine the at least two tail magnitudes of the first pulse.

14. The method of claim 1, wherein predicting the at least two tail magnitudes of the first pulse of the baseline corrected input signal comprises predicting a first tail magnitude occurring at one sampling period following the two or more consecutive samples within the first pulse of the baseline corrected input signal and predicting a second tail magnitude occurring at two sampling periods following the two or more consecutive samples within the first pulse of the baseline corrected input signal.

15. The method of claim 1, wherein creating the one or more look-up tables based on the mathematical pulse model comprises creating the one or more look-up tables based on the mathematical pulse model before reception of the input signal from the medical imaging system.

16. The method of claim 1, wherein the first tail magnitude of the first pulse of the baseline corrected input signal occurs at the same time as the first sample within the second pulse of the baseline corrected input signal, and the second tail magnitude of the first pulse of the baseline corrected input signal occurs at the same time as the second sample within the second pulse of the baseline corrected input signal.

17. The method of claim 1, wherein the mathematical pulse model is $$f(a, t) = a \cdot t^\alpha \cdot e^{-\frac{t}{\tau}},$$

wherein a is the peak magnitude of a pulse, t is time, $\alpha$ is a scaling factor, and $\tau$ is a decay constant.

18. A system comprising at least one processor connected to at least one storage device, wherein the at least one processor is configured to:
create one or more look-up tables based on a mathematical pulse model;
sample a baseline signal at a first predetermined sampling rate to extract two or more consecutive baseline samples;
determine a baseline value based on the two or more consecutive baseline samples;
receive an input signal from a medical imaging system including two or more pulses;
subtract the baseline value from the input signal to form a baseline corrected input signal;
sample the baseline corrected input signal at a second predetermined sampling rate to extract two or more consecutive samples within a first pulse of the baseline corrected input signal;
compare the two or more consecutive samples within the first pulse of the baseline corrected input signal with information stored in the one or more look-up tables to determine the maximum magnitude of the first pulse;
sample the baseline corrected input signal at the second predetermined sampling rate to extract two or more consecutive samples within a second pulse of the baseline corrected input signal, wherein the second pulse of the baseline corrected input signal is temporally subsequent to and at least partially temporally overlaps with the first pulse of the baseline corrected input signal;
predict at least two tail magnitudes of the first pulse of the baseline corrected input signal;
subtract the at least two tail magnitudes of the first pulse of the baseline corrected input signal from the temporally corresponding two or more consecutive samples within the second pulse of the baseline corrected input signal to correct the two or more consecutive samples within the second pulse of the baseline corrected input signal for pileup resulting from the first pulse of the baseline corrected input signal; and
compare the two or more consecutive samples within the second pulse of the baseline corrected input signal with information stored in the one or more look-up tables to determine the maximum magnitude of the second pulse.

19. The system of claim 18, wherein the at least one processor is further configured to:
reconstruct a medical image based on the maximum magnitude of the first pulse and the maximum magnitude of the second pulse; and
enable presentation of the reconstructed medical image.

* * * * *